(12) United States Patent
Han et al.

(10) Patent No.: US 12,123,820 B1
(45) Date of Patent: Oct. 22, 2024

(54) MEMBRANE FOULING EARLY WARNING METHOD AND DEVICE BASED ON MACHINE LEARNING

(71) Applicant: Chongqing University, Chongqing (CN)

(72) Inventors: Le Han, Chongqing (CN); Ting Zou, Chongqing (CN); Jian Liu, Chongqing (CN); Lu Zhou, Chongqing (CN); Haoquan Zhang, Chongqing (CN); Jingmei Yao, Chongqing (CN)

(73) Assignee: Chongqing University, Chongqing (CN)

( * ) Notice: Subject to any disclaimer, the term of this patent is extended or adjusted under 35 U.S.C. 154(b) by 0 days.

(21) Appl. No.: 18/648,343

(22) Filed: Apr. 27, 2024

(30) Foreign Application Priority Data

Apr. 27, 2023 (CN) .......................... 202310474066.3

(51) Int. Cl.
*G01N 15/08* (2006.01)
*B01D 65/10* (2006.01)
(Continued)

(52) U.S. Cl.
CPC ............ *G01N 15/08* (2013.01); *B01D 65/109* (2022.08); *C02F 1/46* (2013.01); *C02F 1/4602* (2013.01);
(Continued)

(58) Field of Classification Search
CPC ........ B01D 65/109; C02F 1/46; C02F 1/4602; G01N 15/08; G01N 15/12;
(Continued)

(56) References Cited

U.S. PATENT DOCUMENTS

2020/0071209 A1  3/2020  Han et al.

FOREIGN PATENT DOCUMENTS

| CN | 108055830 A | 5/2018 |
| CN | 108132340 A | 6/2018 |

(Continued)

OTHER PUBLICATIONS

English translation Chinese Patent Application No. CN 11469273 A (2022).*

(Continued)

*Primary Examiner* — John Kim
(74) *Attorney, Agent, or Firm* — Semicon IP Solutions LLC (57) ABSTRACT

The present application introduces a membrane fouling warning methodology grounded in machine learning. It utilizes a machine learning-based membrane fouling prediction model to automatically forecast and generate electrochemical information values, which characterize the extent of membrane fouling at various time points, based on influent water quality parameters. It then acquires the electrochemical information values $Z_t$ at a moment t and $Z_{t+\Delta t}$ at a moment t+Δt. Subsequently, it computes and assesses the respective fouling levels using the electrochemical information values derived from the membrane fouling prediction model. Finally, it issues an early warning signal contingent upon the determined warning level. This methodology facilitates proactive understanding and management of membrane fouling, thereby sustaining the normal operation of the membrane fouling treatment system, mitigating the propensity for membrane assembly fouling, and prolonging the operational lifespan of the membrane assembly.

8 Claims, 2 Drawing Sheets

(51) Int. Cl.
    *C02F 1/46*    (2023.01)
    *G01N 15/12*   (2024.01)
    *G06F 30/27*   (2020.01)
    *G06N 3/04*    (2023.01)
    *G06N 3/044*   (2023.01)
    *G06N 3/0464*  (2023.01)
    *G06N 3/08*    (2023.01)
    *G06N 20/00*   (2019.01)
    *G16C 20/70*   (2019.01)

(52) U.S. Cl.
    CPC ............ *G01N 15/12* (2013.01); *G06F 30/27* (2020.01); *G06N 3/044* (2023.01); *G06N 3/0464* (2023.01); *G06N 3/08* (2013.01); *G06N 20/00* (2019.01); *G16C 20/70* (2019.02); *G01N 2015/0853* (2013.01)

(58) Field of Classification Search
    CPC ........... G01N 2015/0853; G06N 3/044; G06N 3/0464; G06N 3/08; G06N 20/00; G06F 18/214; G06F 18/241; G06F 30/27; G16C 20/70
    See application file for complete search history.

(56) References Cited

FOREIGN PATENT DOCUMENTS

| | | | |
|---|---|---|---|
| CN | 111948272 | A | 11/2020 |
| CN | 113255764 | A | 8/2021 |
| CN | 114692723 | A | 7/2022 |
| CN | 114943372 | A | 8/2022 |
| CN | 116502530 | B | 11/2023 |
| EP | 2821780 | A1 | 1/2015 |
| JP | 2021020165 | A | 2/2021 |
| KR | 20190113421 | A | 10/2019 |
| WO | WO2023007183 | A1 | 2/2023 |

OTHER PUBLICATIONS

Yun-ping MI, Xiao-ping WANG, Xin Jin, "Water COD Prediction Based on Machine Learning," Journal of Zhejiang University (Engineering Science), vol. 42, No. 5, May 2008, pp. 790-793.

Xiao-ping Wang, Ji-yang Sun, Xin Jin, "Prediction of Water Quality Index in Qiantang River Based on BP neural net work model," Journal of Zhejiang University (Engineering Science), vol. 41, No. 2, Feb. 2007, pp. 361-364.

Notification of First Office Action at National Intellectual Property Administration of the PRC for CN application No. 202310474066.3, issued on Oct. 7, 2023 with English translation (total 6 pages).

Search Report from National Intellectual Property Administration of the PRC for CN application No. 202310474066.3 mailed on Oct. 7, 2023 (total 3 pages).

Notification to Grant Patent Right for Invention from National Intellectual Property Administration of the PRC for CN application No. 202310474066.3 mailed on Oct. 19, 2023 with English translation (total 2 pages).

\* cited by examiner

MEMBRANE FOULING EARLY WARNING METHOD AND DEVICE BASED ON MACHINE LEARNING

CROSS-REFERENCE TO RELATED APPLICATIONS AND INCORPORATION BY REFERENCE

The present application claims the benefit and priority of Chinese patent application No. 202310474066.3 filed on Apr. 27, 2023, and now issued as Chinese Patent CN 116502530B issued on Nov. 7, 2023, all of which are incorporated herein by reference in their entirety.

TECHNICAL FIELD

The present application refers to the technical field of membrane fouling, and particularly refers to a membrane fouling early warning method and a device based on machine learning.

BACKGROUND

Membrane treatment is assuming an increasingly significant role in water treatment, but membrane fouling problems are affecting its application in water treatment. Although the pre-treatment process of influent water in the membrane treatment process is relative mature, the occurrence of membrane fouling is still unavoidable. With the gradual increase in membrane fouling, the flux of the membrane module will be affected. When the pressure difference between the membrane segments accumulates to a set threshold, it is necessary to carry out a downtime chemical cleaning of the membrane module in the membrane treatment system, which has a direct impact on the operational efficiency of the membrane treatment system. Therefore, the need for early warning of fouling of the membrane treatment system is particularly important.

In the prior art, the common method of early warning of the fouling of the membrane treatment system is: setting up a plurality of sensors, collecting a large amount of operating data during the operation of the membrane module, through the data analysis to determine the membrane flux of fouling or the pressure difference between the segments to reach the threshold or limit, and then shut down for chemical cleaning. However, this method has an obvious lag, sometimes may be in the membrane module fouling situation has been very serious to find the problem, and at this time the operating conditions of the membrane module have been affected.

Therefore, it is particularly important to provide early warning before membrane modules are fouled to slow down the fouling trend of membrane modules.

SUMMARY

In view of this, the purpose of the present application is to provide a membrane fouling early warning method, which uses a membrane fouling prediction model constructed based on machine learning, which is capable of automatically predicting (or "identifying") and outputting electrochemical information values used to characterize the degree of membrane fouling at different moments based on the influent water quality parameters of the water to be treated by the membrane, and then calculating and determining the corresponding fouling level based on the electrochemical information values output from the membrane fouling prediction model, and providing early warning tips, which is conducive to timely understanding of membrane fouling in advance to deal with the situation in advance, to maintain the normal operation of the membrane fouling treatment system, to slow down the tendency of fouling of the membrane module, to increase the operating cycle of the membrane module.

The first aspect of the invention discloses a membrane fouling early warning method based on machine learning, which comprises following steps:

constructing a membrane fouling prediction model based on machine learning, which is capable of outputting electrochemical information values used to characterize the fouling level of a membrane treatment system at different moments based on influent water quality parameters, setting a time interval $\Delta t$ for early warning, based on the influent water quality parameters, outputting in advance the electrochemical information values of the membrane treatment system at different moments by means of the constructed said membrane fouling prediction model, from which electrochemical information value $Z_t$ at the moment t and electrochemical information value $Z_{t+\Delta t}$ at the moment $t+\Delta t$ are obtained, calculating a value of the early warning determination formula E:

$$E = \left| \frac{Z_{t+\Delta t} - Z_t}{\Delta t} \right|,$$

when $0 < E < 0.2$, the membrane treatment system is determined to be normal, when $0.2 \leq E < 0.4$, the membrane treatment system is determined to be slightly fouled, corresponding to a slight fouling warning level, when $E \geq 0.4$, the membrane treatment system is determined to be seriously fouled, corresponding to a serious fouling warning level, issuing early warning signal based on the determined warning level.

In the above-described realization process, first, a membrane fouling prediction model is constructed based on machine learning, in which the influent water quality parameters of the water to be treated by the membrane can be used as the input of the membrane fouling prediction model, and the membrane fouling prediction model is capable of outputting electrochemical information values used to characterize the fouling level of a membrane treatment system at different moments based on influent water quality parameters, in which the electrochemical information values include the impedance mode values and/or the interfacial resistance values and the capacitance values. After obtaining the electrochemical information values at different moments, from which electrochemical information value at a certain moment t and electrochemical information value at moment $t+\Delta t$ are obtained, and then value is calculated according to an early warning determination formula, which leads to the corresponding fouling level, then the early warning signal is issued.

According to the membrane fouling early warning method of the present application, by means of the membrane fouling prediction model, the level of fouling that will occur in the membrane treatment system and the corresponding moments can be known at the beginning of the water intake stage. That is, before real-time fouling occurs in the corresponding membrane treatment system, the possibility of membrane fouling can be predicted and forecasted in advance, thereby helping the operator of the membrane treatment system to prepare the relevant operation in advance, in order to maintain the membrane treatment system for the normal operation of water treatment.

Further, the step of issuing warning signal based on the determined warning level comprises:

processing the electrochemical information values at different moments obtained by means of the prediction of said membrane fouling prediction model to acquire corresponding time nodes $T_{slight}$ and $T_{serious}$ at which the slight fouling warning level and the serious fouling warning level will occur, respectively, issuing the early warning signal at a moment $T_{warning}$ prior to the arrival of the acquired time nodes $T_{slight}$ and/or $T_{serious}$.

In the above-described realization process, the final early warning signal is issued at a time prior to the arrival of the corresponding time node of the fouling level predicted by the model, i.e., a moment $T_{warning}$, which can occur prior to the time node $T_{sligjht}$, or prior to the arrival of $T_{serious}$, or at a moment $T_{warning}$ prior to the arrival of both the time node $T_{slight}$ and $T_{serious}$. It will be readily understood by the skilled person that the moment $T_{warning}$ has a time interval (or "time length") from the time nodes $T_{sligjht}$ and $T_{serious}$.

As for the acquisition of the time nodes $T_{slight}$ and $T_{serious}$, it can be obtained through output data of the membrane fouling prediction model or directly with the help of the data processing unit, because, as mentioned before, the membrane fouling prediction model can output the electrochemical information values used to characterize the degree of fouling of the membrane treatment system at different moments based on the influent water quality parameters, and based on the output electrochemical information values related to the slight fouling and serious fouling levels, it is possible to backtrack to obtain their corresponding time nodes.

Further, the method of the present application further comprises the steps as follows:

acquiring a shortest cleaning cycle $D_{cleaning-cycle}$ of membrane treatment system for membrane assembly cleaning, the so-called "acquiring a shortest cleaning cycle $D_{cleaning-cycle}$ of membrane treatment system for membrane assembly cleaning" can be obtained based on previous water plant operating experience and membrane flux, desalination rate and pressure difference changes and other operating parameters for calculation and processing, and also can be obtained directly based on a shortest cleaning cycle $D_{cleaning-cycle}$ preset by the staff of the water plant, which can be realized using the existing technology and shall not be limited herein;

acquiring a moment $T_{slight-warning}$ at which the warning signal corresponding to the slight fouling warning level is to be issued and a moment $T_{serious-warning}$ at which the warning signal corresponding to the serious fouling warning level is to be issued, time periods from zero moment to $T_{slight-warning}$ and $T_{serious-warning}$ are denoted as $D_{slight-warning}$ and $D_{serious-warning}$, respectively, when the shortest cleaning cycle $D_{cleaning-cycle}$ is longer than the time period $D_{serious-warning}$ of serious fouling warning level, it is determined that no pretreatment of the corresponding influent water is required, when the shortest cleaning cycle $D_{cleaning-cycle}$ is shorter than the time period $D_{serious-warning}$ of the serious fouling warning, it is determined that the pretreatment of the corresponding influent water is required, and after pretreatment, acquiring again the corresponding time period $D_{serious-warning}$ for the emergence of the serious fouling warning level by means of the membrane fouling prediction model, until the shortest cleaning cycle $D_{cleaning-cycle}$ is longer than the time period $D_{serious-warning}$ of the serious fouling warning.

The shortest cleaning cycle of the membrane module cleaning can be calculated according to the operating costs that the processor (e.g. water plant) can afford, which can be realized by the existing technology and will not be repeated herein. After calculating the shortest cleaning cycle of the membrane assembly of the corresponding membrane treatment system, it can be input into the control system of the corresponding membrane treatment system, and in the method of the present invention, the shortest cleaning cycle can be obtained by means of an acquisition unit.

The so-called "pretreatment" means that before the wastewater enters into the corresponding membrane treatment system, the influent water quality and/or membrane assembly to be treated by the water treatment method of the existing technology, which can be realized by the existing technology and will not be repeated here. For example, water cleaning can be used for slight fouling and chemical cleaning can be used for serious fouling.

The so-called "when the shortest cleaning cycle $D_{cleaning-cycle}$ is longer than the time period $D_{serious-warning}$ of serious fouling warning" refers to the comparison of the time period (or time length) counting from current moment (i.e., the "zero moment") at which the time node $T_{serious}$ of the serious fouling early warning is acquired to the arrival of the time node $T_{serious}$ of the serious fouling early warning with the shortest cleaning cycle $D_{cleaning-cycle}$. When the shortest cleaning cycle $D_{cleaning-cycle}$ is longer than the time period $D_{serious-warning}$ of the arrival of the time node $T_{serious}$ of the serious fouling early warning, the corresponding influent does not need to be pre-treated. On the contrary, when the shortest cleaning cycle $D_{cleaning-cycle}$ is shorter than the time period $D_{serious-warning}$ of the arrival of the time node $T_{serious}$ of the serious fouling early warning, it is necessary to pretreatment of the corresponding influent. And after pretreatment of the influent water to be treated by the membrane, based on the water quality parameters of the influent water after pretreatment, acquiring again the corresponding time node $T_{serious}$ for the emergence of the serious fouling warning level by means of the membrane fouling prediction model, and if the shortest cleaning cycle $D_{cleaning-cycle}$ is shorter than the time period of the arrival of the time node $T_{serious}$ of the serious fouling early warning, then it is still necessary to carry out a pretreatment of the corresponding influent water. Repeating the foregoing process, until the shortest cleaning cycle $D_{cleaning-cycle}$ is longer than the time period $D_{serious-warning}$ of the serious fouling warning.

Further, the step of constructing a membrane fouling prediction model based on machine learning comprises:

acquiring influent water quality parameters of influent samples under different influent water quality conditions to form a sample set of influent water quality parameters, acquiring a data set of electrochemical information values of the corresponding membrane treatment system changed with respect to time under said different influent water quality conditions to form a sample set of electrochemical information values, combining the acquired sample set of influent water quality parameters with said sample set of electrochemical information values to create a combined sample set, based on the combined sample set, characterizing the influent water quality parameters therein to extract the key water quality factors in the influent water quality parameters that caused significant change in the electrochemical information values of the membrane treatment system with respect to time, wherein the term "significant change" refers to the change that occurs when the aforementioned early warning determination formula E>0.4 applied, using the extracted key water quality factors and moments as independent variables, and using the electrochemical information values corresponding to each moment and used to characterize the fouling level of the membrane treatment system as dependent variables, to train the original model, performing model evaluation for the model obtained by training to obtain said membrane fouling prediction model.

In the present application, the determination of influent water quality parameters of influent samples under different influent water quality conditions and the determination of electrochemical information values changed with respect to time is performed based on the corresponding specific membrane process conditions. Based on this, the construction of the model is also performed based on the corresponding specific membrane process conditions. The so-called "specific membrane process conditions" refers to a specific type of membrane treatment system. That is to say, in the present invention, the establishment of the membrane fouling early warning model corresponds to the corresponding specific membrane process conditions, and in the industrial practical application, the database and the corresponding membrane fouling prediction model can be further established based on the collection of water quality parameters and electrochemical information values of different membrane process systems of the processor (including the type and characteristics of the membrane materials selected by the processor). For example, for reverse osmosis, ultrafiltration, or nanofiltration selected by the processor, a membrane fouling warning model based on the characteristics of reverse osmosis, ultrafiltration, or nanofiltration membranes can be established for fouling early warning, and a membrane fouling warning model based on the characteristics of hydrophobic membranes can be established for membrane distillation, and so on. If the processor selects a mixed type of membrane treatment system, the determination of parameters and the construction of models can be carried out on the basis of the selected mixed type membrane treatment system, so as to be able to be used for the fouling early warning of the mixed-type membrane treatment system.

The so-called "combining the acquired sample set of influent water quality parameters with said sample set of electrochemical information values" means that the sample set of influent water quality parameters obtained and the sample set of electrochemical information values of the corresponding membrane treatment system obtained under the corresponding water quality conditions are combined based on the correspondence between them.

In the process of model selection and establishment, the parameters in the sample set of influent water quality parameters are firstly characterized by the key factor assessment method in order to find the key factors that cause significant changes in the electrochemical information values (impedance modulus Z or interface resistance value R and capacitance value C), i.e., the key factors that affect the degree and rate of membrane fouling. The key factor assessment enables the multi-dimensional dataset (i.e., the combined sample sets) to be dimensionality reduced and denoised in order to extract the key elements for the construction of the model. The extracted key water quality factors and moments are used as inputs for the independent variables, and the electrochemical information values characterizing the degree of membrane fouling and corresponding to each moment are used as outputs for the dependent variables.

Additionally, after determining the key water quality factors affecting the electrochemical information values of the membrane treatment system to change significantly with respect to time through the key factor assessment method, it is possible to consider the extracted key water quality factors when the shortest cleaning cycle $D_{cleaning-cycle}$ is shorter than the time period $D_{serious-warning}$ of the serious fouling warning and when it is necessary to carry out the pretreatment of the corresponding influent water, that is, when pretreatment of the corresponding influent water is required, the key water quality factors that have been extracted will be taken into consideration for pretreatment.

In the realization of the above steps for obtaining the sample set of electrochemical information values, the potentiostat is first used to monitor the impedance values Z of the membrane assembly. The specific method is to release a perturbation signal (e.g., AC voltage 100 mV) to the membrane assembly, and scan the full spectrum of the membrane module during operation in the frequency range of $10^{-3}$-$10^{6}$ Hz to obtain the impedance value of the membrane with respect to time and the Nyquist plots at different frequencies. Then the correlation discrimination method or the equivalent circuit method is used to obtain the impedance data (impedance mode Z) or the electrochemical component signals (interface resistance value R and capacitance value C) change curves with respect to time under different process operating conditions. The specific steps refer to the following description of the embodiment when the electrochemical information value is the impedance mode value and the embodiment when the electrochemical information value is the interface resistance value and the capacitance value. In the present invention, the term "different process operating conditions" refers to different parameter conditions for a specific type (or "a certain type") of membrane. In an embodiment, the electrochemical information values are impedance mode values, then the step of acquiring a data set of electrochemical information values of the corresponding membrane treatment system changed with respect to time under different influent water conditions comprises:

monitoring and acquiring impedance data (i.e., impedance mode under full spectral sweep) of membrane assembly in the membrane treatment system at different frequencies changed with respect to time by using a potentiostat, based on the impedance data acquired from the potentiostat at different frequencies, performing a correlation discriminant analysis for impedance mode values acquired at each frequency at each moment and the monitored membrane assembly parameters, to acquire the frequencies corresponding to the impedance mode values with discriminant coefficient $r^2$>0.9, performing fixed-frequency measurements by means of the potentiostat at said frequencies with discriminant coefficient $r^2$>0.9, to acquire a data set of impedance mode values of the impedance mode values changed with respect to time under the fixed-frequency measurements, as said electrochemical information values sample set.

In this embodiment, the impedance data set of the impedance mode values changed with respect to time under constant frequency measurement is obtained by means of the correlation discrimination method. Specifically, based on the impedance data obtained by the potentiostat at different frequencies, a matrix of impedance values changed with time at the same frequency is established, and Pearson's correlation analysis is used to determine the correlation between the change of the impedance values with respect to time at the same frequency and the conventional parameters of the membrane process. The specific method is to calculate the ratio of the product of the covariance of the impedance values matrix and the membrane process parameter and the standard deviation of the two at the same frequency, to obtain the correlation coefficient r, and to retain the frequency value corresponding to the correlation coefficient $r^2>0.9$. The potentiostat is used to perform fixed-frequency measurements at frequency values of $r^2>0.9$ to obtain the impedance mode data sets of the impedance mode values Z with respect to time, and then establish a database B. In the present invention, the membrane process parameters include but are not limited to, membrane flux, transmembrane pressure difference (TMP), and the like.

The correlation discriminant method could directly measure the impedance mode values at constant frequency, which is easy to operate, and the process of data processing is relatively simple.

In another embodiment, the electrochemical information values are interfacial resistance values and capacitance values, step of acquiring a data set of electrochemical information values changed with respect to time of the corresponding membrane treatment system under different influent conditions comprises:

monitoring and acquiring impedance data of membrane assembly in the membrane treatment system at different frequencies changed with respect to time by using the potentiostat, constructing an equivalent circuit model based on the impedance data acquired from the potentiostat at different frequencies, according to the equivalent circuit model, establishing a data set of electrochemical component signals of the interfacial resistance and capacitance values of circuit elements changed with respect to time as said electrochemical information values sample set, wherein the circuit elements represent the membrane surface (external/outer) fouling layer and the membrane bulk (internal/material body) fouling layer.

In this embodiment, the specific method is to build a system of different series and parallel electrochemical elements to represent the membrane and solution, respectively, by analyzing the impedance data measured by the potentiostat. Least squares fitting was used to select an equivalent circuit with a fitting error of less than 1% as the equivalent circuit model and its circuit element composition suitable for analyzing membrane fouling dynamics. The electrochemical signal values representing the circuit elements of the surface membrane fouling layer and the bulk membrane layer were established based on the equivalent circuit model, and the electrochemical information values (interface resistance values R and capacitance values C) of the circuit elements of the equivalent circuit model was obtained as data sets of electrochemical element signals with respect to time.

Through the equivalent circuit method, the electrochemical signals of each membrane layer that can be analyzed based on the equivalent circuit fitting can reflect the fouling of each layer of the membrane, which is more indicative.

Further, the step of performing model evaluation for the model obtained by training to obtain said membrane fouling prediction model comprises:

using regression coefficient $R^2$ as an evaluation metric to assess the regression performance of the model, and the calculating formula of the regression coefficient $R^2$ is as follows:

$$R^2 = 1 - \frac{\sum_{i=1}^{n}(y_i - \hat{y}_i)^2}{\sum_{i=1}^{n}(y_i - \bar{y})^2},$$

where y is the actual value, $\hat{y}$ is the predicted value, and $\bar{y}$ is the average of all actual values, $R^2 \in [0,1]$ and the AUC value is used as an indicator for assessing the categorical performance of the model, comprising:

data classification based on predicted data from trained models, based on the classification results, calculating the recall TPR and FPR of the model, and obtaining the ROC curve by plotting the FPR as the x-axis and the TPR as the y-axis to obtain the AUC value of the data, identifying the model with a relatively large AUC value as the described membrane fouling prediction model.

Further, the original model is selected from one of following models: regression model, random forest model, support vector machine model, feed-forward neural network model, and recurrent neural network model.

The second aspect of the invention discloses a membrane fouling prediction device based on machine learning, the membrane fouling prediction device comprises:

a model constructing unit, configured to construct a membrane fouling prediction model based on machine learning, which is capable of outputting electrochemical information values used to characterize fouling level of a membrane treatment system at different moments based on influent water quality parameters, a warning time setting unit, configured to set the time interval $\Delta t$ for early warning, a prediction unit, configured to, based on the influent water quality parameters, outputting in advance electrochemical information values of membrane treatment system at different moments by means of the constructed said membrane fouling prediction model, from which electrochemical information value $Z_t$ at the moment t and electrochemical information value $Z_{t+\Delta t}$ at the moment t+$\Delta t$ are obtained, respectively, a calculating unit, configured to calculate a value of early warning determination formula E:

$$E = \left| \frac{Z_{t+\Delta t} - Z_t}{\Delta t} \right|,$$

when 0<E<0.2, the membrane treatment system is determined to be normal, when 0.2≤E<0.4, the membrane treatment system is determined to be slightly fouled, corresponding to slight fouling warning level, when E≥0.4, the membrane treatment system is determined to be seriously fouled, corresponding to the serious fouling warning level, an early warning unit, configured to issue early warning signal based on the determined warning level.

Further, the membrane fouling prediction device further comprises:

a first acquiring unit, configured to process the electrochemical information values at different moments obtained by means of the prediction of said membrane fouling prediction model to acquire corresponding time nodes $T_{slight}$ and $T_{serious}$ at which the slight fouling warning level and the serious fouling warning level will occur, respectively, said early warning unit is configured to issue the early warning signal at a moment $T_{warning}$ prior to the arrival of the acquired time nodes $T_{slight}$ and/or $T_{serious}$, said membrane fouling prediction device further comprises:

a second acquiring unit, configured to acquire a shortest cleaning cycle $D_{cleaning\text{-}cycle}$ of membrane treatment systems for membrane assembly cleaning, a third acquiring unit, configured to acquire a moment $T_{slight\text{-}warning}$ at which the warning signal corresponding to the slight fouling warning level is to be issued and a moment $T_{serious\text{-}warning}$ at which the warning signal corresponding to the serious fouling warning level is to be issued, and to denote time periods from moment zero to $T_{slight\text{-}warning}$ and $T_{serious\text{-}warning}$ as $D_{slight\text{-}warning}$ and $D_{serious\text{-}warning}$, respectively, a comparing and determining unit, configured to compare the shortest cleaning cycle $D_{cleaning\text{-}cycle}$ with the serious fouling warning time period $D_{serious\text{-}warning}$, and to determine whether a pretreatment is required, when the shortest cleaning cycle $D_{cleaning\text{-}cycle}$ is longer than the time period $D_{serious\text{-}warning}$ of the serious fouling warning level, it is determined that no pretreatment of corresponding influent water is required, when the shortest cleaning cycle $D_{cleaning\text{-}cycle}$ is shorter than the time period $D_{serious\text{-}warning}$ of the serious fouling warning, it is determined that the pretreatment of the corresponding influent water is required, after the pretreatment of the corresponding influent water, the third acquiring unit acquires again the corresponding time period $D_{serious\text{-}warning}$ for the emergence of serious fouling warning level by means of the membrane fouling prediction model, the comparing and determining unit compares the shortest cleaning cycle $D_{cleaning\text{-}cycle}$ with newly acquired time period $D_{serious\text{-}warning}$ of the serious fouling warning, until the shortest cleaning cycle $D_{cleaning\text{-}cycle}$ is longer than the time period $D_{serious\text{-}warning}$ of the serious fouling warning.

Further, the membrane fouling prediction device further comprises:

the fourth acquiring unit, configured to acquire influent water quality parameters of influent samples under different influent water quality conditions to form a sample set of influent water quality parameters, the fifth acquiring unit, configured to acquire a data set of electrochemical information values of the corresponding membrane treatment system changed with respect to time under said different influent water quality conditions to form a sample set of electrochemical information values, a sample combining unit, configured to combining the acquired sample set of influent water quality parameters with said sample set of electrochemical information values to create a combined sample set, a key water quality factor extraction unit, configured to, based on the combined sample set, characterizing the influent water quality parameters therein to extract the key water quality factors in the influent water quality parameters that caused significant changes in the electrochemical information values of the membrane treatment system with respect to time, a training unit, configured to train the original model by using the extracted key water quality factors and moments as independent variables, and using the electrochemical information values corresponding to each moment and used to characterize the fouling level of the membrane treatment system as dependent variables, a model evaluation unit, configured to perform a model evaluation for the model obtained by training to obtain said membrane fouling prediction model.

Further, said electrochemical information values are impedance mode values, or said electrochemical information values are interface resistance values and capacitance values.

The third aspect of the present invention discloses an electronic device, the electronic device comprising a memory and a processor, the memory for storing a computer program, the processor running the computer program to cause the electronic device to perform the membrane fouling warning method disclosed in the first aspect of the present invention.

The fourth aspect of the present application discloses a readable storage medium, the readable storage medium having computer program instructions stored therein, the computer program instructions, when read and run by a processor, executing the membrane fouling warning method disclosed in the first aspect of this application.

Beneficial effect: in the membrane fouling early warning method of the present application, a membrane fouling prediction model constructed based on machine learning is used, which is capable of automatically predicting (or "identifying") and outputting electrochemical information values used to characterize the degree of membrane fouling at different moments based on the influent water quality parameters of the water to be treated by the membrane, and then calculating and determining the corresponding fouling level based on the electrochemical information values output from the membrane fouling prediction model, and providing early warning tips, which is conducive to timely understanding of membrane fouling in advance to deal with the situation in advance, to maintain the normal operation of the membrane fouling treatment system, to slow down the tendency of fouling of the membrane module, to increase the operating cycle of the membrane module.

BRIEF DESCRIPTION OF THE DRAWINGS

The membrane fouling early warning method of the application is disclosed in detail below in conjunction with the embodiments shown in the accompanying drawings and the accompanying markings.

DETAILED DESCRIPTION

The technical solutions of the present application will be clearly and completely described below in conjunction with the accompanying drawings. It is clear that the described embodiments are only a part of this application and not all of the embodiments. Based on the embodiments of the present application, all other embodiments obtained by a skilled person in the art without making creative labor will fall within the scope of protection of the present application.

It should be noted that all directional indications (such as up, down, left, right, forward, back . . . ) in the embodiments of the present application are used only for explaining the relative positional relationship, movement, etc., among the various components in a particular attitude (as shown in the accompanying drawings). The directional indications change accordingly if the particular attitude is changed.

Furthermore, expressions involving "first", "second", and the like in this application are used for descriptive purposes only and are not to be understood as indicating or implying their relative importance or implicitly specifying the number of technical features indicated. As a result, a feature defined as "first" or "second" may include at least one such feature, either explicitly or implicitly. In addition, the technical solutions between the various embodiments can be combined with each other, but it must be based on the fact that the person of ordinary skill in the field can realize it, and when the combination of technical solutions is contradictory or unattainable, it should be considered that the combination of such technical solutions does not exist, and is not within the scope of protection of the claims of the present application.

Embodiment 1

Figure 1:
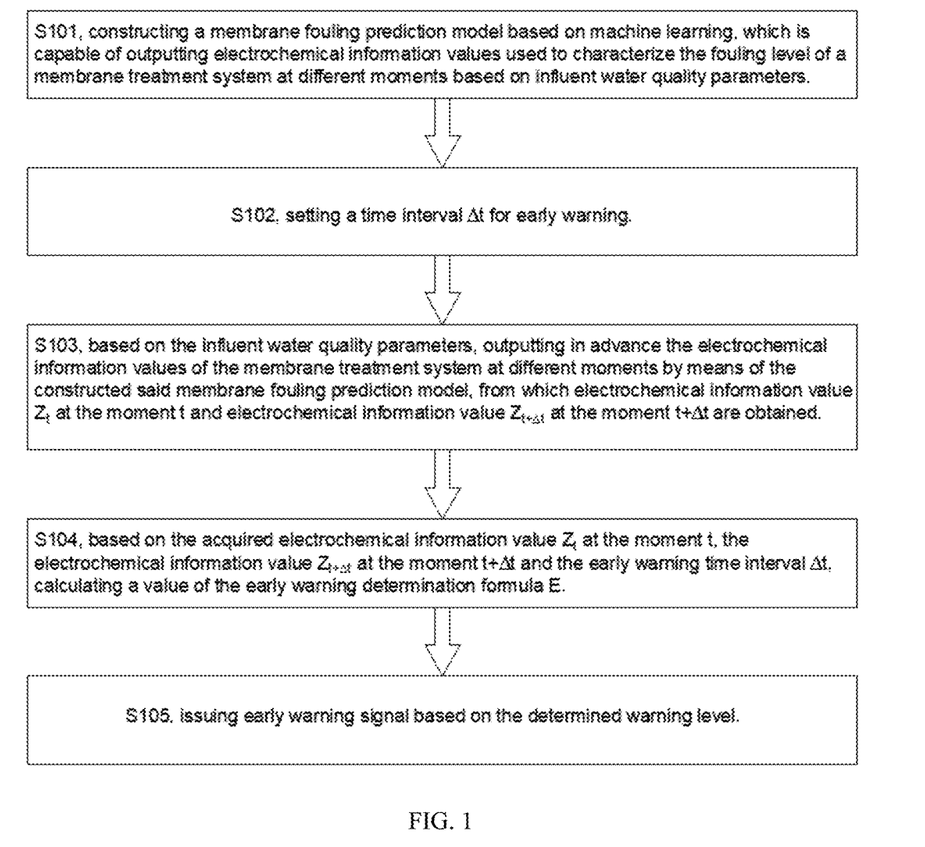
FIG. 1 illustrates a flowchart of the steps of the membrane fouling early warning method of the present application.

FIG. 1 illustrates a flowchart of the steps of the membrane fouling early warning method of the present application. Wherein the membrane fouling early warning method comprises:

S101, constructing a membrane fouling prediction model based on machine learning, which is capable of outputting electrochemical information values used to characterize the fouling level of a membrane treatment system at different moments based on influent water quality parameters.

In the embodiment of the present application, the influent water quality parameters can be $COD_{Cr}$ (chemical oxygen demand), TOC (total organic carbon), $NH_3$—N (ammonia nitrogen), TP (total phosphorus), TN (total nitrogen), which can be obtained by existing conventional monitoring methods or by measurement using sensors related to the corresponding parameters, to which embodiments of the present application are not limited. The electrochemical information values refer to impedance mode values or interface resistance values and capacitance values.

In the embodiment of the present application, the membrane fouling prediction model can be one of regression model, random forest model, support vector machine model, feed-forward neural network model and recurrent neural network model. As a preferred embodiment, the deep learning neural network (CNN) model is selected as the membrane fouling prediction model.

S102, setting the time interval $\Delta t$ for early warning. In this embodiment, step S102 occurs after step S101, but it should be understood that step S102 is also capable of occurring before step S101.

In the embodiment of the present application, the early warning time interval $\Delta t$ can be set according to the operator. The range of early warning time interval $\Delta t$ can be from 24 hours to 48 hours, preferably, 24 hours, 36 hours, or 48 hours.

S103, based on the influent water quality parameters, outputting in advance the electrochemical information values of the membrane treatment system at different moments by means of the constructed said membrane fouling prediction model, from which electrochemical information value $Z_t$ at the moment t and electrochemical information value $Z_{t+\Delta t}$ at the moment $t+\Delta t$ are obtained.

In the embodiment of the present application, the moment t refers to a moment in all moments after the start of predicting the electrochemical information value of the membrane treatment system by means of the membrane fouling prediction model based on the influent water quality parameter, and the moment $t+\Delta t$ refers to a moment counted from moment t plus the warning time interval $\Delta t$.

Before step S103, it further includes the step of obtaining the influent water quality parameters of the water body to be treated, and the specific method can be achieved by a conventional monitoring method, for example, by a corresponding sensor, to which embodiments of the present application are not limited.

S104, based on the acquired electrochemical information value $Z_t$ at the moment t, the electrochemical information value $Z_{t+\Delta t}$ at the moment $t+\Delta t$ and the early warning time interval $\Delta t$, calculating a value of the early warning determination formula E:

$$E = \left| \frac{Z_{t+\Delta t} - Z_t}{\Delta t} \right|,$$

when $0<E<0.2$, the membrane treatment system is determined to be normal, when $0.2 \leq E < 0.4$, the membrane treatment system is determined to be slightly fouled, corresponding to a slight fouling warning level, when $E \geq 0.4$, the membrane treatment system is determined to be seriously fouled, corresponding to a serious fouling warning level.

S105, issuing early warning signal based on the determined warning level.

In the embodiment of the present application, different colors correspond to different fouling warning levels, and preferably, the slight fouling warning level is a yellow warning, while the serious fouling warning level can be shown as a red warning.

In the embodiment of the present application, the execution subject of the method could be a computing device such as a computer, a server, or a hardware device with a processing chip, for which is not limited in the present application.

In the embodiment of the present application, the execution subject of the method could also be a smart device such as a smart phone, a tablet computer, etc., for which is not limited in the present application.

In practice, due to the constructed membrane fouling prediction model is capable of outputting electrochemical information values used to characterize the fouling level of a membrane treatment system at different moments based on influent water quality parameters, the level of fouling that will occur in the membrane treatment system and the corresponding moments can be known by means of the membrane fouling prediction model at the beginning of the water intake stage, thereby helping the operator of the membrane treatment system to prepare the relevant operation in advance, in order to maintain the membrane treatment system for the normal operation of water treatment.

In this embodiment, the step S105 of issuing early warning signal based on the determined warning level comprises:

S501, processing the electrochemical information values at different moments obtained by means of the prediction of said membrane fouling prediction model to acquire corresponding time nodes $T_{slight}$ and $T_{serious}$ at which the slight fouling warning level and the serious fouling warning level will occur, respectively.

S502, issuing the early warning signal at a moment $T_{warning}$ prior to the arrival of the acquired time nodes $T_{slight}$ and/or $T_{serious}$.

In this embodiment, the moment $T_{warning}$ is prior to the arrival of the acquired time node $T_{slight}$ or $T_{serious}$, that is, the moment $T_{warning}$ has a time interval with the acquired time node $T_{slight}$ or $T_{serious}$, which is able to be taken from the range of 1-60 minutes, preferably 30 minutes, 15 minutes or 10 minutes.

In alternative embodiment, it is also possible to set up the warning signal to be issued at the moment $T_{warning}$ prior to the arrival of the acquired time node $T_{slight}$ or $T_{serious}$.

It should be understood by one skilled in the art that if the time period (or "time length") starting from current moment at which the time nodes $T_{slight}$ and $T_{serious}$ are acquired to the arrival of the time nodes $T_{slight}$ and $T_{serious}$ is shorter than the predetermined moment $T_{warning}$, a warning signal will be directly issued according to the present method.

In this embodiment, the membrane fouling warning method of the present application further comprises the following steps:

S106, acquiring a shortest cleaning cycle $D_{cleaning-cycle}$ for membrane assembly cleaning in membrane treatment systems.

S107, acquiring a moment $T_{slight-warning}$ at which the warning signal corresponding to the slight fouling warning level is to be issued and a moment $T_{serious-warning}$ at which the warning signal corresponding to the serious fouling warning level is to be issued, time periods from zero moment to $T_{slight-warning}$ and $T_{serious-warning}$ are denoted as $D_{slight-warning}$ and $D_{serious-warning}$, respectively, the implementation process of step S107 can be performed independently or can be directly realized based on the implementation process of the aforementioned step S501.

S108, when the shortest cleaning cycle $D_{cleaning-cycle}$ is longer than the time period $D_{serious-warning}$ of serious fouling warning level, it is determined that no pretreatment of the corresponding influent water is required, when the shortest cleaning cycle $D_{cleaning-cycle}$ is shorter than the time period $D_{serious-warning}$ of the serious fouling warning, it is determined that the pretreatment of the corresponding influent water is required.

S109, pretreatment of influent water when pre-treatment is required, acquiring again the corresponding time node $T_{serious}$ for the emergence of the serious fouling warning level by means of the membrane fouling prediction model, until the shortest cleaning cycle $D_{cleaning-cycle}$ is longer than the time period $D_{serious-warning}$ of the serious fouling warning. That is, the steps of S107 and S108 are repeated post-pretreatment until the shortest cleaning cycle $D_{cleaning-cycle}$ is longer than the time period $D_{serious-warning}$ for serious fouling warning.

This judgment process establishes criteria for determining the necessity of pretreating the feed water, enhancing the practicability of membrane fouling treatment. Furthermore, it allows for pretreatment to occur prior to the arrival of time node of the membrane fouling warning level, independent of real-time membrane fouling occurrences or severity.

In the embodiment of the present application, key water quality factors that influence the degree and rate of membrane fouling are extracted and utilized as primary criteria for pretreating the influent water, thereby enhancing the standardization of membrane fouling warning.

In the embodiment of the present application, the step of constructing a membrane fouling prediction model based on machine learning comprises:

S201, acquiring influent water quality parameters of influent samples under different influent water quality conditions to form a sample set of influent water quality parameters.

In the embodiment of the present application, various parameters of the influent water from different influent water quality conditions, such as $COD_{Cr}$ (Chemical Oxygen Demand), TOC (Total Organic Carbon), $NH^3$—N(Ammonia Nitrogen), TP (Total Phosphorus), TN (Total Nitrogen), and others, can be gathered through conventional monitoring practices. These collected parameters are then summarized as influent water quality parameters. Different influent water quality conditions refer to variations in the parameters of the influent water, as previously described.

S202, acquiring a data set of electrochemical information values of the corresponding membrane treatment system changed with respect to time under aforestated different influent water quality conditions to form a sample set of electrochemical information values. That is, the electrochemical information data of the membrane treatment system corresponding to the influent samples under the currently conducted conditions were obtained under different influent conditions.

Figure 2:
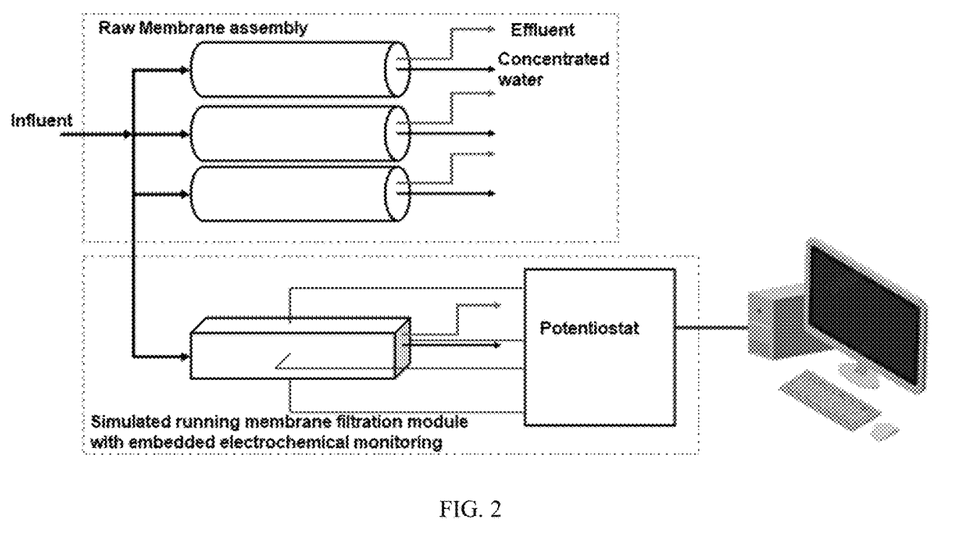
FIG. 2 illustrates a schematic diagram of monitoring membrane assembly using the potentiostat in the present application.

In the embodiment of the present application, the potentiostat is used to measure the electrochemical information (including impedance mode value Z, interface resistance value R, and capacitance value C), for characterizing the degree and rate of membrane fouling under different influent conditions.

It operates as described below: 1) a set of simulated membrane filtration (EIS Canary Cell) modules with embedded electrochemical monitoring is connected in parallel with a large-scale membrane treatment system, which maintains the same operating conditions (filtration, water production, cleaning, etc.) as the large-scale membrane system, and four AC impedance spectral output input probes are installed in the modules, which are connected to the potentiostat and a computer for real-time recording and transmission of the transmission data and analyses.

2) the potentiostat is used to monitor the impedance mode values Z of the simulated membrane filtration module by releasing a disturbance signal (e.g., AC voltage of 100 mV) to the EIS canary cell, and then scanning the full spectrum of the simulated membrane filtration module in the range of $10^{-3} \sim 10^6$ Hz to obtain the impedance value of the membrane with respect to time and the Nyquist diagram for different frequency cases. The impedance data (impedance mode values Z) or electrochemical component signals (interfacial resistance R and capacitance C) under different membrane process operating conditions were obtained as output data by using the correlation discrimination method or the equivalent circuit model method (one of them is sufficient for practical engineering).

S203, combining the acquired sample set of influent water quality parameters with said sample set of electrochemical information values to create a combined sample set. That is, combine the aforementioned sample set of influent water quality parameters with the corresponding sample set of electrochemical information values (either impedance modulus sample set or component information sample set, such as interfacial resistance R and capacitance C sample set) obtained under different influent conditions to form a joint sample set for subsequent key factor analysis and the construction of the machine learning model.

S204, based on the combined sample set, characterizing the influent water quality parameters therein to extract the key water quality factors in the influent water quality parameters that caused significant changes in the electrochemical information values of the membrane treatment system with respect to time.

S205, using the extracted key water quality factors and moments as independent variables, and using the electrochemical information values corresponding to each moment and used to characterize the fouling level of the membrane treatment system as dependent variables, to train the original model.

S206, performing model evaluation for the model obtained by training to obtain said membrane fouling prediction model.

For the preceding step S202, in the case where the values of mentioned electrochemical information are impedance mode values, the step of acquiring a data set of electrochemical information values of the corresponding membrane treatment system changed with respect to time under different influent water conditions comprises:

monitoring and acquiring impedance data (i.e., impedance modulus under full spectral sweep) of membrane assembly in the membrane treatment system at different frequencies changed with respect to time by using the potentiostat, based on the impedance data acquired from the potentiostat at different frequencies, preforming a correlation discriminant analysis for impedance mode values acquired at each frequency at each moment and the monitored membrane assembly parameters, to acquire the frequencies corresponding to the impedance mode values with discriminant coefficient $r^2>0.9$, performing fixed-frequency measurements by means of the potentiostat at said frequencies with discriminant coefficient $r^2>0.9$, to acquire a data set of impedance mode values of the impedance mode values changed with respect to time under the fixed-frequency measurements, as said electrochemical information values sample set.

In the case where said electrochemical information values are interfacial resistance values and capacitance values, said step of acquiring a data set of electrochemical information values changed with respect to time of the corresponding membrane treatment system under different influent conditions comprises:

monitoring and acquiring impedance data of membrane assembly in the membrane treatment system at different frequencies changed with respect to time by using the potentiostat, constructing an equivalent circuit model based on the impedance data acquired from the potentiostat at different frequencies, according to the equivalent circuit model, establishing a data set of electrochemical component signals of the interfacial resistance and capacitance values of circuit elements changed with respect to time as said electrochemical information values sample set, wherein the circuit elements represent the membrane surface (external/outer) fouling layer and the membrane bulk (internal/material body) fouling layer.

For the aforementioned step S204, the parameters in the sample set of influent water quality parameters are characterized by the key factor assessment method to find the key factors that cause significant changes in the electrochemical information values (impedance mode Z or interfacial resistance value R and capacitance value C), i.e., the key factors that affect the degree and rate of membrane fouling.

Specifically, the parameters in the sample set of influent water quality parameters are characterized using the partial least squares method to find the key factors that cause significant changes in the impedance mode values Z or the interfacial resistance value R and the capacitance value C (i.e., affecting the speed and degree of membrane fouling), so as to achieve the purpose of dimensionality reduction and denoising of the multi-dimensional database and extracting the elements for the establishment of the model.

Taking the aforementioned electrochemical information value as the interface resistance value R and capacitance value C as an embodiment, the combined sample set is the influent water quality parameter sample set plus electrochemical element signal dataset, in which the data source of the independent variable matrix X is the influent water quality parameter sample set, and the electrochemical element signal (interfacial resistance value R and capacitance value C) dataset of the dependent variable Y. The main steps to carry out the assessment of the key factors are:

step a, let the number of samples be n and the number of independent variables be p, then the matrix of independent variables is:

$$X = (x_1, x_2 \ldots x_n) = \begin{pmatrix} x_{11} & \cdots & x_{1p} \\ \vdots & \ddots & \vdots \\ x_{n1} & \cdots & x_{np} \end{pmatrix},$$

standardizing the independent variable matrix X and the dependent variable matrix Y:

$$x_{ij}^* = \frac{(x_{ij} - \mu_j^{(1)})}{s_{x_j}} i = 1, 2, \ldots, n; j = 1, 2, \ldots, p,$$

$$y_{ik}^* = \frac{(y_{ik} - \mu_k^{(2)})}{s_{y_k}} i = 1, 2, \ldots, n; k = 1, 2,$$

where $x_{ij}$、$x^*_{ij}$ are the values of the independent variables before and after standardization, $y_{ik}$、$y^*_{ik}$ are the values of the dependent variables before and after standardization. $\mu_j^{(1)}$、$\mu_k^{(2)}$ are the means of $x_j$ and $y_k$, $s_{x_j}$、$s_{y_k}$ are the standard deviations of $x_j$ and $y_k$, to obtain the standard deviation matrices $E_0$, $F_0$.

Step b, determining the number of key factors $x_h$. The defining equation for the cross validity $Q_h^2$ of $x_h$ is as follows:

$$Q_h^2 = 1 - \frac{S_{PRESS,h}}{S_{ss,h-1}} = 1 - \frac{\sum_{i=1}^n (y_i - \hat{y}_{h(-i)})^2}{\sum_{i=1}^n (y_i - \hat{y}_{hi})^2},$$

where $Q_h^2$ is the cross validity coefficient, which is an indicator for evaluating the predictive power of the fitted equation, $S_{PRESS,h}$ is the sum of squares of the prediction errors of Y, $S_{ss,h-1}$ is for the variance fitting error with h−1 components fitted with all the sample points, $y_i$ is the measured data, $y_{hi}$ is the fitted value of $y_i$ obtained by modelling using h principal components, $y_{h(-i)}$ is the fitted value of $y_i$ obtained by modelling using h principal components after removing the $i^{th}$ measured data is the fitted value of $y_i$ obtained using h principal components modelling after removing the $i^{th}$ measured data.

When the value of $Q_h^2$ exceeds 0.0975, it is considered that the addition of the $h^{th}$ principal component has significantly improved the model accuracy, and it is necessary to continue extracting the principal components. Until the value of $Q_h^2$ is less than the specified value, it is considered that the component cannot explain the model better. For embodiment, for the fourth component $Q_h^2 \geq 0.0975$, it is considered that the fourth component explains the model better, and for the fifth component $Q_h^2<0.0975$, it is considered that the fifth component does not explain the model better.

Step c, the extraction of the key factor $x_h$:

the expression for $x_h$ is as follows:

$$X_h = E_0 w_h^*$$
$$w_h^* = \prod_{j=1}^{h-1}(I - w_j p_j^T) w_h;$$
$$p_j = \frac{E_{j-1}^T t_j}{\|t_j\|^2},$$

where $w_h$ is the eigenvector corresponding to the largest eigenvalue of matrix $E_{h-1}^T F_0 F_0^T E_{h-1}$, $E_i$ is the residual vector of the same order as $t_i$ and for any, $t_i^T E_i=0$, I is the unit matrix.

As can be appreciated by a person skilled in the art, in the case where the joint sample set is a sample set of influent water quality parameters plus a sample set of impedance mode data, the analyses for carrying out an assessment of the critical water quality factors are the same as in the case where the joint sample set described above is a sample set of influent water quality parameters plus a data set of signals from electrochemical components.

With respect to step S205, in embodiments of the present application, alternative models include a regression model, a random forest model, a support vector machine model, a feedforward neural network model, a recurrent neural network model, and the like.

In a preferred embodiment, a deep learning neural network (CNN) model is built. The electrochemical information values used in this embodiment are impedance modal values (i.e., the composition of the joint sample set is a sample set of influent water quality parameters+an impedance modal value dataset, the number of key water quality factors (or known as key water quality indicators) obtained after the aforementioned key factor assessment analysis is 5, recorded as x1, x2, x3, x4, x5; and the neural network comprises a hidden layer with a number of neural nodes in this hidden layer is three.

The model consists of three layers, i.e. one input layer, one hidden layer and one output layer. The number of neurons in the input layer is 5, the number of neural nodes in the hidden layer is 3, and the number of neurons in the output layer is 1. The model is connected in a 5-3-1 manner (the number of hidden layers and the number of nodes in the hidden layer of the neural network can be varied according to the actual requirements). 80% of the total data set in the joint sample set is selected as the training set and the remaining 20% as the validation set. The input data of the input layer at the moment t is $x=[x_1, x_2, x_3, x_4, x_5]$, where $x_1, x_2, x_3, x_4, x_5$ are the monitoring data of the extracted key water quality indicators $x_1, x_2, x_3, x_4, x_5$, and the output layer is the impedance mode values Z corresponding to the corresponding moment t. The computation of the various layers of the prediction model is shown below:

1) Input Layer, which has Five Neurons, and the Output Value of this Layer is:

μ=x, where $\mu=[\mu_1, \mu_2, \mu_3, \mu_4, \mu_5]$, which has dimension 1×5.

2) Hidden Layer, which has Three Neural Nodes, and the Output of this Layer is:

$$\theta = \frac{1}{1 + e^{-(w_{0,1}\mu + b_1)}},$$

where $\theta=[\theta_1, \theta_2, \theta_3]$, which has dimension 1×3. $w_{0,1}$ denotes the weight vector between the input layer and the first hidden layer at the moment t, $b_1$ denotes the bias vector of the first hidden layer at the moment t, and the dimension of the values $w_{0,1}$ of and $b_1$ is 5×3.

3) Output Layer, which has Only One Neuron, and the Output of this Layer is:

$$z = \frac{1}{1 + e^{-(w_{1,2}\theta + b_2)}},$$

where z has a dimension of 3×1. $w_{1,2}$ denotes the weight vector between the first hidden layer and the output layer at the moment t, $b_2$ denotes the bias vector of the output layer at the moment t, $w_{1,2}$ and $b_2$ takes a dimension of 3×1.

Regarding step S206, the regression coefficient ($R^2$) is selected as the evaluation index for assessing the regression nature of the model, and the AUC value (Area under the Curve of ROC, or "Area under the Curve of ROC") is selected as the evaluation index for assessing the categorization nature of the model, and the errors of the model are evaluated by combining the two parameters. The two parameters are combined to evaluate the error of the model and select the best model that meets the actual situation. The formula for calculating the regression coefficient ($R^2$) is shown below:

$$R^2 = 1 - \frac{\sum_{i=1}^{n}(y_i - \hat{y}_i)^2}{\sum_{i=1}^{n}(y_i - \bar{y})^2},$$

where y is the actual value, $\hat{y}$ is the predicted value, and $\bar{y}$ is the average of all actual values. $R^2 \in [0,1]$ And, based on the data results, the data is categorized as follows:

| matrix confusion | | Forecast category | |
| --- | --- | --- | --- |
| | | Positive | Negative |
| Actual category | Positive | TP (True Positive) | FN (False Negative) |
| | Negative | FP (False Positive) | TN (True Negative) |

The recall TPR (True Positive Rate) and FPR (False Positive Rate) of the prediction model were calculated as follows:

$$TPR = \frac{TP}{(TP + FN)},$$
$$FPR = \frac{FP}{(FP + TN)}.$$

Drawing the graph with FPR as x-axis and TPR as y-axis, the ROC curve (Receiver operating characteristic curve) was obtained, so as to find the AUC value of the data (AUC ∈ [0.5,1]), the AUC value can be very intuitively evaluated the model's goodness, and its value is generally between 0.5 and 1 The larger the value, the higher the model fitness, the model is selected as the subsequent membrane fouling prediction model.

Embodiment 2

The present application further discloses a membrane fouling prediction device based on machine learning, comprising:
- a model constructing unit, configured to construct a membrane fouling prediction model based on machine learning, which is capable of outputting electrochemical information values used to characterize fouling level of a membrane treatment system at different moments based on influent water quality parameters,
- a warning time setting unit, configured to set the time interval $\Delta t$ for early warning,
- a prediction unit, configured to, based on the influent water quality parameters, outputting in advance electrochemical information values of membrane treatment system at different moments by means of the constructed said membrane fouling prediction model, from which electrochemical information value $Z_t$ at the moment t and electrochemical information value $Z_{t+\Delta t}$ at the moment t+$\Delta t$ are obtained, respectively,
- a calculating unit, configured to calculate a value of early warning determination formula E:

$$E = \left| \frac{Z_{t+\Delta t} - Z_t}{\Delta t} \right|,$$

when $0 < E < 0.2$, the membrane treatment system is determined to be normal, when $0.2 \leq E < 0.4$, the membrane treatment system is determined to be slightly fouled, corresponding to slight fouling warning level, when $E \geq 0.4$, the membrane treatment system is determined to be seriously fouled, corresponding to the serious fouling warning level,
- an early warning unit, configured to issue early warning signal based on the determined warning level.

In this embodiment, the membrane fouling prediction device further comprises:
- a first acquiring unit, configured to process the electrochemical information values at different moments obtained by means of the prediction of said membrane fouling prediction model to acquire corresponding time nodes $T_{slight}$ and $T_{serious}$ at which the slight fouling warning level and the serious fouling warning level will occur, respectively, said early warning unit is configured to issue the early warning signal at a moment $T_{warning}$ prior to the arrival of the acquired time nodes $T_{slight}$ and/or $T_{serious}$, said membrane fouling prediction device further comprises:
- a second acquiring unit, configured to acquire a shortest cleaning cycle $D_{cleaning\text{-}cycle}$ of membrane treatment systems for membrane assembly cleaning,
- a third acquiring unit, configured to acquire a moment $T_{slight\text{-}warning}$ at which the warning signal corresponding to the slight fouling warning level is to be issued and a moment $T_{serious\text{-}warning}$ at which the warning signal corresponding to the serious fouling warning level is to be issued, and to denote time periods from moment zero to $T_{slight}$-warning and $T_{serious\text{-}warning}$ as $D_{slight\text{-}warning}$ and $D_{serious\text{-}warning}$, respectively,
- a comparing and determining unit, configured to compare the shortest cleaning cycle $D_{cleaning\text{-}cycle}$ with the serious fouling warning time period $D_{serious\text{-}warning}$, and to determine whether a pretreatment is required,
- when the shortest cleaning cycle $D_{cleaning\text{-}cycle}$ is longer than the time period $D_{serious\text{-}warning}$ of the serious fouling warning level, it is determined that no pretreatment of corresponding influent water is required,
- when the shortest cleaning cycle $D_{cleaning\text{-}cycle}$ is shorter than the time period $D_{serious\text{-}warning}$ of the serious fouling warning, it is determined that the pretreatment of the corresponding influent water is required,
- after the pretreatment of the corresponding influent water, the third acquiring unit acquires again the corresponding time period $D_{serious\text{-}warning}$ for the emergence of serious fouling warning level by means of the membrane fouling prediction model, the comparing and determining unit compares the shortest cleaning cycle $D_{cleaning\text{-}cycle}$ with newly acquired time period $D_{serious\text{-}warning}$ of the serious fouling warning, until the shortest cleaning cycle $D_{cleaning\text{-}cycle}$ is longer than the time period $D_{serious\text{-}warning}$ of the serious fouling warning.

In this embodiment, the membrane fouling prediction device further comprises:
- the fourth acquiring unit, configured to acquire influent water quality parameters of influent samples under different influent water quality conditions to form a sample set of influent water quality parameters,
- the fifth acquiring unit, configured to acquire a data set of electrochemical information values of the corresponding membrane treatment system changed with respect to time under said different influent water quality conditions to form a sample set of electrochemical information values,
- a sample combining unit, configured to combine the acquired sample set of influent water quality parameters with said sample set of electrochemical information values to create a combined sample set,
- a key water quality factor extraction unit, configured to, based on the combined sample set, characterizing the influent water quality parameters therein to extract the key water quality factors in the influent water quality parameters that caused significant changes in the electrochemical information values of the membrane treatment system with respect to time,
- a training unit, configured to train the original model by using the extracted key water quality factors and moments as independent variables, and using the electrochemical information values corresponding to each moment and used to characterize the fouling level of the membrane treatment system as dependent variables,
- a model evaluation unit, configured to perform a model evaluation for the model obtained by training to obtain said membrane fouling prediction model, In this embodiment, the electrochemical information values are impedance mode values or the electrochemical information values are interface resistance and capacitance values.

The present application further discloses an electronic device, the electronic device comprising a memory and a processor, the memory for storing a computer program, the processor running the computer program to cause the electronic device to perform the membrane fouling warning method disclosed in the embodiment 1 of the present application.

The recent application further discloses a readable storage medium, the readable storage medium having computer program instructions stored therein, the computer program instructions, when read and run by a processor, executing the membrane fouling warning method disclosed in the embodiment 1 of the present application.

In the several embodiments provided in this application, it should be understood that the devices and methods disclosed, may also be realized in other ways. The device embodiments described above are merely schematic, for embodiment, the flowcharts and block diagrams in the accompanying drawings show the architecture, functionality, and operation that may be achieved by the devices, methods, and computer program products according to several embodiments of the present application. At this point, each box in the flowchart or block diagram may represent a module, program segment, or portion of code, described module, program segment, or portion of code comprising one or more executable instructions for carrying out a specified logical function. It should also be noted that in some implementations as substitutions, the functions indicated in the boxes may also occur in a different order than those indicated in the accompanying drawings. For embodiment, two consecutive boxes can actually be executed substantially in parallel, and they can sometimes be executed in reverse order, depending on the function involved. It should also be noted that each box in the block diagram and/or flowchart, as well as combinations of boxes in the block diagram and/or flowchart, may be implemented with a specialized hardware-based system that performs the specified function or action, or may be implemented with a combination of specialized hardware and computer instructions.

In addition, the various functional modules in various embodiments of the present application may be integrated together to form a separate part, or the individual modules may stand alone, or two or more modules may be integrated to form a separate part.

Described functionality may be stored in a computer-readable storage medium if it is implemented in the form of a software function module and sold or used as a stand-alone product. Based on this understanding, the technical solution of the present application may be embodied in the form of a software product, which is essentially or in part a contribution to the prior art, or part of the technical solution may be embodied in the form of a software product that is stored in a storage medium and comprises a number of instructions to cause a computer device (which may be a personal computer, a server, or a network device, etc.) to carry out all or part of the steps of the method described in the various embodiments of the present application. The computer software product is stored in a storage medium comprising several instructions to cause a computer device (which may be a personal computer, a server, or a network device, etc.) to perform all or part of the steps of the method described in various embodiments of the present application. The aforementioned storage medium includes a USB flash drive, a removable hard disk, a read-only memory (ROM, Read-Only Memory), a random-access memory (RAM, Random Access Memory), a diskette or a CD-ROM, and other media that can store program code.

The foregoing are only embodiments of the present application and are not intended to limit the scope of protection of the present application, which may be subject to various changes and variations for those skilled in the field. Any modifications, equivalent substitutions, improvements, etc. made within the spirit and principles of this application shall be included in the scope of protection of this application. It should be noted that similar symbols and letters denote similar items in the following accompanying drawings, and therefore, once an item is defined in an accompanying drawing, no further definition or explanation of it is required in the subsequent accompanying drawings.

The foregoing is only a specific embodiment of the present application, but the scope of protection of the present application is not limited herein, and any changes or substitutions that can be readily thought of by any person skilled in the field within the scope of the technology disclosed in the present application shall be covered by the scope of protection of the present application. Therefore, the scope of protection stated in this application shall be subject to the scope of protection of the claims.

It is to be noted that, in this document, relational terms such as first and second are used only to distinguish one entity or operation from another, and do not necessarily require or imply any such actual relationship or order between those entities or operations. Furthermore, the terms "including", "comprising", or any other variant thereof, are intended to cover non-exclusive inclusion, such that a process, method, article, or apparatus comprising a set of elements includes not only those elements, but also other elements not expressly listed, or other elements that are not expressly listed for the purpose of such a process, method, article or apparatus, or other elements that are not expressly listed for the purpose of such a process, method, article or equipment. elements, or also includes elements that are inherent to such process, method, article or apparatus. Without further limitation, the fact that an element is defined by the phrase "includes a . . . " does not preclude the existence of additional identical elements in the process, method, article, or apparatus that includes described element.

What is claimed is:

1. A membrane fouling early warning method based on machine learning, wherein the method comprises the steps of:

constructing a membrane fouling prediction model based on machine learning, which is capable of outputting electrochemical information values at different moments based on influent water quality parameters, for characterizing a fouling level of a membrane treatment system;

setting a time interval $\Delta t$ for an early warning;

outputting in advance the electrochemical information values of the membrane treatment system at the different moments, based on the influent water quality parameters, by means of the constructed membrane fouling prediction model, from which an electrochemical information value $Z_t$ at a moment t and an electrochemical information value $Z_{t+\Delta t}$ at a moment t+$\Delta t$ are obtained;

calculating a determination value E of the early warning according to formula:

$$E = \left| \frac{Z_{t+\Delta t} - Z_t}{\Delta t} \right|,$$

wherein, when 0<E<0.2, the membrane treatment system is determined to be normal; when 0.2≤E<0.4, the membrane treatment system is determined to be slightly fouled, corresponding to a slight fouling warning level; and when E≥0.4, the membrane treatment system is determined to be seriously fouled, corresponding to a serious fouling warning level; and issuing an early warning signal based on the determined warning level, wherein the step of constructing the membrane fouling prediction model based on machine learning comprises:

acquiring the influent water quality parameters of influent samples under different influent water quality conditions to form a sample set of the influent water quality parameters;

acquiring a data set of the electrochemical information values of a corresponding membrane treatment system changed with respect to time under the different influent water quality conditions to form a sample set of the electrochemical information values;

combining the acquired sample set of the influent water quality parameters with the sample set of the electrochemical information values to create a combined sample set;

characterizing the influent water quality parameters based on the combined sample set, to extract key water quality factors in the influent water quality parameters that cause significant changes in the electrochemical information values of the membrane treatment system with respect to time;

training an original model, by using the extracted key water quality factors and moments as independent variables and by using the electrochemical information values, which correspond to each moment and are used to characterize the fouling level of the membrane treatment system, as dependent variables; and performing model evaluation for a model obtained by the training to obtain the membrane fouling prediction model, wherein:

the electrochemical information values are impedance mode values; or the electrochemical information values are interface resistance values and capacitance values.

2. The membrane fouling early warning method based on machine learning according to claim 1, wherein the step of issuing the early warning signal based on the determined warning level comprises:

processing, at the different moments, the electrochemical information values obtained by means of prediction of the membrane fouling prediction model to acquire corresponding time nodes $T_{slight}$ and $T_{serious}$ at which the slight fouling warning level and the serious fouling warning level will occur, respectively; and issuing the early warning signal at a moment $T_{warning}$ prior to arrival of the acquired time nodes $T_{slight}$ and/or $T_{serious}$.

3. The membrane fouling early warning method based on machine learning according to claim 1, wherein the method further comprises following steps:

acquiring a shortest cleaning cycle $D_{cleaning-cycle}$ for membrane assembly cleaning in membrane treatment systems;

acquiring a moment $T_{slight-warning}$ at which the early warning signal corresponding to the slight fouling warning level is to be issued and a moment T serious-warning at which the early warning signal corresponding to the serious fouling warning level is to be issued, wherein time periods from zero moment to $T_{slight-warning}$ and $T_{serious-warning}$ are denoted as time periods $D_{slight-warning}$ and $D_{serious-warning}$, respectively;

determining that no pretreatment of a corresponding influent water is required if the shortest cleaning cycle $D_{cleaning-cycle}$ is longer than the time period $D_{serious-warning}$ of the serious fouling warning level;

determining that the pretreatment of the corresponding influent water is required if the shortest cleaning cycle $D_{cleaning-cycle}$ is shorter than the time period $D_{serious-warning}$ of the serious fouling warning; and acquiring again, after the pretreatment, the corresponding time period $D_{serious-warning}$ for an emergence of the serious fouling warning level by means of the membrane fouling prediction model, until the shortest cleaning cycle $D_{cleaning-cycle}$ is longer than the time period $D_{serious-warning}$ of the serious fouling warning.

4. The membrane fouling early warning method based on machine learning according to claim 1, wherein:

if the electrochemical information values are the impedance mode values, the step of acquiring the data set of the electrochemical information values of the corresponding membrane treatment system changed with respect to time under the different influent water quality conditions comprises:

monitoring and acquiring, by using a potentiostat, impedance data of a membrane assembly in the membrane treatment system at different frequencies, the impedance data changing with respect to time;

performing, based on the impedance data acquired by using the potentiostat at the different frequencies, a correlation discriminant analysis between the impedance mode values at each frequency and each moment and monitored parameters of the membrane assembly, to acquire frequencies corresponding to the impedance mode values with a discriminant coefficient $r^2>0.9$; and performing fixed-frequency measurements by means of the potentiostat at the frequencies with the discriminant coefficient $r^2>0.9$, to acquire a data set of the impedance mode values, changing with respect to time under the fixed-frequency measurements, as the sample set of the electrochemical information values; and if the electrochemical information values are the interfacial resistance values and the capacitance values, the step of acquiring the data set of the electrochemical information values changed with respect to time of the corresponding membrane treatment system under the different influent conditions comprises:

monitoring and acquiring, by using the potentiostat, impedance data of the membrane assembly in the membrane treatment system at the different frequencies, the impedance data changing with respect to time;

constructing an equivalent circuit model based on the impedance data acquired from the potentiostat at different frequencies; and establishing, according to the equivalent circuit model, a data set of electrochemical component signals of interfacial resistance values and capacitance values of circuit elements, which change with respect to time, as the sample set of the electrochemical information values, wherein the circuit elements represent a membrane surface fouling layer and a membrane bulk fouling layer.

5. The membrane fouling early warning method based on machine learning according to claim 4, wherein the step of performing the model evaluation for the model obtained by the training to obtain the membrane fouling prediction model comprises:

using a regression coefficient $R^2$ as an evaluation metric to assess a regression performance of the model, wherein a calculating formula of the regression coefficient $R^2$ is as follows:

$$R^2 = 1 - \frac{\sum_{i=1}^{n}(y_i - \hat{y}_i)^2}{\sum_{i=1}^{n}(y_i - \bar{y})^2},$$

wherein y is an actual value; $\hat{y}$ is a predicted value; $\bar{y}$ is an average of all actual values; and $R^2 \in [0,1]$; and using an AUC (Area under the Curve) value as an assessing indicator for a categorical performance of the model, comprising:
classifying data based on predicted data from a trained model;
calculating, based on the classified data, recall rates TPR (True Positive Rate) and FPR (False Positive Rate) of the trained model;
obtaining an ROC (Receiver Operating Characteristic) curve by plotting the FPR as an x-axis and the TPR as a y-axis, to obtain the AUC value of the classified data; and
determining the trained model having a relatively large AUC value as the membrane fouling prediction model.

6. The membrane fouling early warning method based on machine learning according to claim 5, wherein the original model is selected from one of following models: regression model, random forest model, support vector machine model, feed-forward neural network model, and recurrent neural network model.

7. A membrane fouling prediction device based on machine learning, comprising:
a model constructing unit, configured to construct a membrane fouling prediction model based on machine learning, which is capable of outputting electrochemical information values at different moments based on influent water quality parameters, for characterizing a fouling level of a membrane treatment system;
a warning time setting unit, configured to set a time interval $\Delta t$ for an early warning;
a prediction unit, configured to output in advance the electrochemical information values of the membrane treatment system at the different moments, based on the influent water quality parameters, by means of the constructed membrane fouling prediction model, from which an electrochemical information value Z at a moment t and an electrochemical information value $Z_{t+\Delta t}$ at a moment $t+\Delta t$ are obtained, respectively;
a calculating unit, configured to calculate a determination value E of the early warning according to formula:

$$E = \left| \frac{z_{t+\Delta t} - z_t}{\Delta t} \right|,$$

Wherein, when 0<E<0.2, the membrane treatment system is determined to be normal; when 0.2≤E<0.4, the membrane treatment system is determined to be slightly fouled, corresponding to a slight fouling warning level; and when E≥0.4, the membrane treatment system is determined to be seriously fouled, corresponding to a serious fouling warning level;

an early warning unit, configured to issue an early warning signal based on the determined warning level;
a fourth acquiring unit, configured to acquire the influent water quality parameters of influent samples under different influent water quality conditions to form a sample set of the influent water quality parameters;
a fifth acquiring unit, configured to acquire a data set of the electrochemical information values of the corresponding membrane treatment system changed with respect to time under the different influent water quality conditions to form a sample set of the electrochemical information values;
a sample combining unit, configured to combine the sample set of the influent water quality parameters with the sample set of the electrochemical information values to create a combined sample set;
a key water quality factor extraction unit, configured to characterize, based on the combined sample set, the influent water quality parameters therein to extract key water quality factors in the influent water quality parameters that cause significant changes in the electrochemical information values of the membrane treatment system with respect to time, a training unit, configured to train an original model by using the extracted key water quality factors and moments as independent variables and using the electrochemical information values, which correspond to each moment and are used to characterize the fouling level of the membrane treatment system, as dependent variables; and
a model evaluation unit, configured to perform model evaluation for a model obtained by the training to obtain the membrane fouling prediction model,
wherein the electrochemical information values are impedance mode values, or interface resistance values and capacitance values.

8. The membrane fouling prediction device according to claim 7, further comprising:
a first acquiring unit, configured to process, at different moments, the electrochemical information values obtained by means of prediction of the membrane fouling prediction model, to acquire corresponding time nodes $T_{slight}$ and $T_{serious}$ at which the slight fouling warning level and the serious fouling warning level will occur, respectively, wherein the early warning unit is configured to issue the early warning signal at a moment $T_{warning}$ prior to an arrival of the acquired time nodes $T_{slight}$ and/or $T_{serious}$;
a second acquiring unit, configured to acquire a shortest cleaning cycle $D_{cleaning\text{-}cycle}$ of membrane treatment systems for membrane assembly cleaning;
a third acquiring unit, configured to acquire a moment $T_{slight\text{-}warning}$ at which the early warning signal corresponding to the slight fouling warning level is to be issued and a moment $T_{serious\_warning}$ at which the early warning signal corresponding to the serious fouling warning level is to be issued, and configured to denote time periods from zero moment to $T_{slight\text{-}warning}$ and $T_{serious\text{-}warning}$ as time periods $D_{slight\text{-}warning}$ and $D_{serious\text{-}warning}$, respectively; and
a comparing and determining unit, configured to compare the shortest cleaning cycle $D_{cleaning\text{-}cycle}$ with the time period $D_{serious\text{-}warning}$ of the serious fouling warning level and configured to determine whether a pretreatment is required, wherein:
the comparing and determining unit is configured to determine that no pretreatment of a corresponding influent water is required if the shortest cleaning cycle $D_{cleaning-cycle}$ is longer than the time period $D_{serious-warning}$ of the serious fouling warning level;

the comparing and determining unit is configured to determine that the pretreatment of the corresponding influent water is required if the shortest cleaning cycle $D_{cleaning-cycle}$ is shorter than the time period $D_{serious-warning}$ of the serious fouling warning level;

the third acquiring unit is configured to acquire again, after the pretreatment of the corresponding influent water, a corresponding time period $D_{serious-warning}$ for an emergence of the serious fouling warning level by means of the membrane fouling prediction model; and the comparing and determining unit is configured to compare the shortest cleaning cycle $D_{cleaning-cycle}$ with newly acquired time period $D_{serious-warning}$ of the serious fouling warning level, until the shortest cleaning cycle $D_{cleaning-cycle}$ is longer than the time period $D_{serious-warning}$ of the serious fouling warning level.

* * * * *